(12) United States Patent
Huang et al.

(10) Patent No.: US 7,625,999 B2
(45) Date of Patent: Dec. 1, 2009

(54) METHOD FOR TESTING THE ABILITY OF AN AGENT TO INHIBIT FIBROBLAST GROWTH FACTOR BINDING WITH LABELED HEPARAN SULFATE

(75) Inventors: Kuo-Sen Huang, Livingston, NJ (US); Anthony Neri, El Granada, CA (US); John Lawson Roberts, Budd Lake, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 603 days.

(21) Appl. No.: 11/444,057

(22) Filed: May 31, 2006

(65) Prior Publication Data
US 2006/0216777 A1 Sep. 28, 2006

Related U.S. Application Data

(62) Division of application No. 10/314,683, filed on Dec. 9, 2002, now Pat. No. 7,081,351.

(60) Provisional application No. 60/341,573, filed on Dec. 18, 2001.

(51) Int. Cl.
    *C07K 17/00* (2006.01)
(52) U.S. Cl. .................................... 530/350; 536/1.11
(58) Field of Classification Search ........................ None
    See application file for complete search history.

(56) References Cited

U.S. PATENT DOCUMENTS

| | | | |
|---|---|---|---|
| 4,859,581 | A | 8/1989 | Nicolson et al. |
| 5,206,223 | A | 4/1993 | Vlodavsky et al. |
| 5,332,812 | A | 7/1994 | Nicolson et al. |
| 5,362,641 | A | 11/1994 | Fuks et al. |
| 5,795,860 | A | 8/1998 | Witt et al. |
| 5,849,722 | A | 12/1998 | Habuchi et al. |
| 5,891,655 | A | 4/1999 | Ornitz |
| 5,968,822 | A | 10/1999 | Pecker et al. |
| 6,190,875 | B1 | 2/2001 | Ben-Artzi et al. |
| 6,207,402 | B1 | 3/2001 | Freeman et al. |

FOREIGN PATENT DOCUMENTS

| | | |
|---|---|---|
| DE | 199 55 803 | 5/2001 |
| EP | 0 244932 | 11/1987 |
| JP | S62-265998 | 11/1987 |
| JP | P H09-40581 | 2/1997 |
| WO | WO 93/19096 | 9/1993 |
| WO | WO 94/20512 | 9/1994 |
| WO | WO 95/04158 | 2/1995 |
| WO | WO 98/03638 A1 | 1/1998 |
| WO | WO 99/40207 | 8/1999 |
| WO | WO 99/43830 | 9/1999 |
| WO | WO 00/03036 | 1/2000 |
| WO | WO 00/77241 A3 | 12/2000 |

OTHER PUBLICATIONS

Lider et al., J. Clin. Invest., 83, pp. 752-756 (1989).
Willenberg et al., J. Immunol., 140, pp. 3401-3405 (1988).
Hemmila et al., Anal. Biochem., 137, pp. 335-343 (1984).
Hemmila et al., Drug Discovery Today, 2, pp. 373-381 (1997).
Vlodavsky, et al., Invasion Metastasis, 14, pp. 290-302 (1994).
Freeman, C. & Parish, C.R., Biochem J., 325, pp. 229-23 (1997).
Parish, C.R., et al., Cancer Res., 59, pp. 3433-3441 (1999).
Nakajima, M., et al., Anal Biochem., 157 91), pp. 162-17 (1986).
Oosta, G.M., et al., Biol. Chem., 257 (19), pp. 11249-11255 (1982).
Sewell, R.F., et al., Biochem J., 264 (3), pp. 777-783 (1989).
Maccaranna, M., et al., 268 (32), pp. 23898-23905 (1993).
Aviezer, D., et al., J. Biomol. Screen., 6(3), pp. 171-177 (2001).
Kardami, et al., Developmental Biology, vol. 126, pp. 19-28 (1988).
Foxall, et al., Journal of Cellular Physiology, vol. 168, pp. 657-667 (1996).
Chernousov & Carey, Journal of Biological Chemistry, vol. 268, pp. 16810-16814 (1993).
Berman, et al., Journal of Biological Chemistry, vol. 274, pp. 36132-36138 (1993).
Foxall et al., Anal. Biochem., 231, pp. 366-373 (1995).
Toyoshima et al., J. Biol. Chem., 274, pp. 24153-21460 (1999).
Yamane, Y. et al, *Jour. Of Bio. Chem.*, 273(13) 7375-7381 (1998).
Germani, Y. et al, *Jour. Of Immuno. Methods*, 146, 25-32 (1992).

*Primary Examiner*—Sandra Saucier
*Assistant Examiner*—Susan Hanley
(74) *Attorney, Agent, or Firm*—George W. Johnston; Patricia S. Rocha-Tramaloni; David E. Wildman

(57) ABSTRACT

The present invention provides a method for testing an agent for its ability to inhibit binding between fibroblast growth factor (FGF) and heparan sulfate, comprising the steps of: interacting in solution immobilized FGF on a solid support with the agent and labeled heparan sulfate, and detecting the presence or absence of label in the solution remote from the solid support.

1 Claim, 13 Drawing Sheets

METHOD FOR TESTING THE ABILITY OF AN AGENT TO INHIBIT FIBROBLAST GROWTH FACTOR BINDING WITH LABELED HEPARAN SULFATE

PRIORITY TO RELATED APPLICATIONS

This application is a division of application Ser. No. 10/314,683, filed Dec. 9, 2002, now allowed; which claims the benefit of U.S. Provisional Application No. 60/341,573, filed Dec. 18, 2001. The entire contents of the above-identified applications are hereby incorporated by reference.

BACKGROUND OF THE INVENTION

Heparan sulfate (HS) and heparan sulfate proteoglycans (HSPG) are present in the extracellular matrix (ECM) as well as on the cell surface. They play an important role in regulating cellular processes such as cell adhesion, migration, differentiation and proliferation (1-3). In addition, they interact with many molecules including growth factors (e.g. fibroblast growth factors and platelet-derived growth factor), cytokines, extracellular matrix proteins, lipoproteins, and β-amyloid proteins (2, 4-8). Release of these proteins by proteases or glycosidases provides a regulatory mechanism for induction of growth, chemotaxis, and extravasation of cells in normal and disease processes (3, 5).

Heparanase is an endo-(-D)-glucuronidase that degrades heparan sulfate proteoglycans (HSPG) at specific sites. Its activity has been detected in a number of cell types including human platelets, fibroblasts, neutrophils, activated T-lymphocytes, monocytes and human umbilical vein endothelial cells (HUVEC) (9-12). In addition, elevated levels of heparanase are associated with melanoma and other types of tumor cells (13-16). Evidence suggests that cleavage of the HS chains from HSPG by heparanase leads to the disassembly of the ECM and facilitates cell migration. It is an important process in the tissue invasion by blood-borne malignant tumor cells and leucocytes (14, 17-19). In fact, treatment of experimental animals with heparanase inhibitors considerably reduced the incidence of lung metastases (20-22), indicating that heparanase inhibitors may be applied to inhibit tumor cell invasion and metastasis.

The ability of activated lymphocytes, macrophages and granulocytes to penetrate ECM and migrate to target tissues was found to be dependent on heparanase activity (23). In response to various activation signals (e.g., immune complexes, antigens, nitrogens), heparanase is released from intracellular compartments (e.g., lysosomes, specific granules), suggesting its involvement in inflammatory and autoimmune responses. Treatment of experimental animals with heparanase inhibitors markedly reduced the incidence of T-cell mediated delayed-type hypersensitivity, experimental autoimmune encephalomyelitis and adjuvant arthritis (23-24), indicating that heparanase inhibiting compounds may be applied to inhibit autoimmune and inflammatory diseases.

Thus, heparanase plays an important role in the degradation of the extracellular matrix. It is implicated in inflammation, tumor angiogenesis and metastasis. Despite evidence implicating the attractiveness of heparanase as a therapeutic target for intervention, drug development has been hampered by the lack of a high throughput method for testing the ability of agents to inhibit heparanase activity.

Heparanase assays have been performed using radiolabeled ECM-associated HSPG (34-35). Radiolabeled material released from the ECM by heparanase cleavage is detected. Disadvantages include that proteases are often required to expose HS chains for heparanase degradation. Gel filtration analysis is difficult to adopt for high throughput. The use of radiolabeled material involves the disposition of material in accordance with safety standards.

Satoh et al. (32) report methods to covalently link oligosaccharides to methyl vinyl ether-maleic anhydride copolymer (MMAC) coated microtiter plates. These methods are cumbersome because they require several chemical reactions to link oligosaccharides onto MMAC coated plates. Some of the organic reagents and solvents may destroy microtiter plates. Furthermore, the overall yield could be very low after several steps of chemical reactions.

Freeman and Parish report a rapid method for measuring heparanase activity (27). Chicken histidine-rich glycoprotein (cHRG) was coupled to Sepharose and used for isolating undigested HS. Although the method separates heparanase-cleaved products from the HS substrate, the method requires large amounts of cHRG-Sepharose to quantitatively deplete undigested HS from the reaction mixtures. Also, the handling of Sepharose beads in connection with column chromatography and centrifugation methods does not lend itself to high throughput screening.

Ben-Artzi et al. (33) report a high throughput assay for measuring heparanase activity. Using HS or certain types of heparin species as a substrate, the heparanase reaction is carried out in 96 well microtiter plates and stopped by the addition of tetrazolium blue. The tetrazolium blue reacts with the reactive ends of sugars exposed by heparanase cleavage. The number of cleavages of the substrate is measured calorimetrically. The assay requires the use of large amounts of HS as substrate (50 µg HS per 100 µl) and at least a 2 hour heparanase incubation period (2-24 hrs). These requirements of the assay, though not procedurally optimal, provide conditions that favor cleavage of sugars of the HS substrate. The measurement of greater numbers of reactive sugars is necessary to compensate to some extent for the low signal to background ratio. A further drawback of the assay stems from the use of tetrazolium salt which is reactive with many types of groups, and can thus cause inaccurate results. Purity of assay reagents and test compounds is therefore a concern.

Heparanase catalytic activity could also be inhibited indirectly by an agent that prevents or alters heparanase substrate binding to FGF. Because such agents can potentially block FGF mediated cell signaling events, they are potential candidates as therapeutic agents for cancer and diseases caused by abnormal neovascularization (31).

SUMMARY OF THE INVENTION

The present invention provides a method for testing an agent for its potential to inhibit heparanase catalytic activity, comprising the steps of:

interacting immobilized heparanase substrate binding protein on a solid support with labeled heparanase substrate to provide immobilized labeled heparanase substrate, interacting a heparanase enzyme solution with the immobilized labeled heparanase substrate in the presence of the agent, and detecting the presence or absence of label in the solution remote from the solid support, to determine whether or not the agent has the potential to inhibit heparanase.

The labeled heparanase substrate may be bound to an immobilization bridge which binds to immobilized molecules on a solid support, to provide bridge-immobilized labeled heparanase substrate.

The present invention also provides method for testing an agent for its ability to inhibit binding between fibroblast growth factor (FGF) and heparanase substrate, comprising the steps of:

interacting in solution immobilized FGF on a solid support with the agent and labeled heparanase substrate, and detecting the presence or absence of label in the solution remote from the solid support, to determine whether or not the agent has the ability to inhibit binding between fibroblast growth factor and heparanase substrate.

DETAILED DESCRIPTION OF THE INVENTION

Figure 1A:
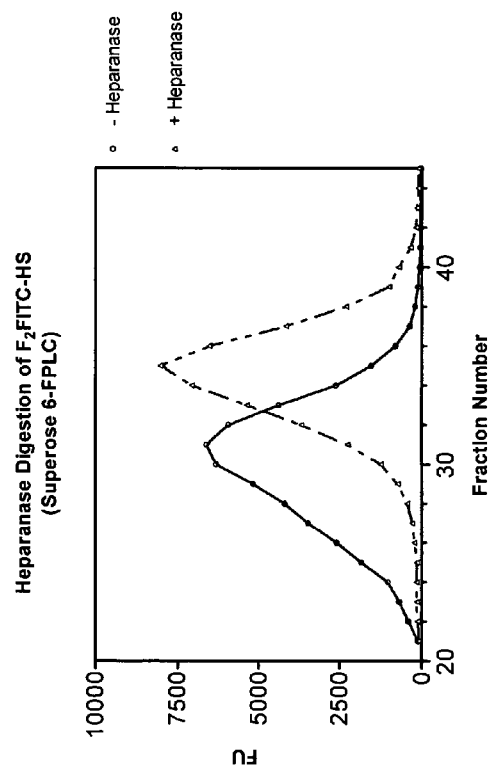
FIG. 1A graphically shows the products of heparanase digestion of $F_2$FITC-HS eluted from a Superose 6-FPLC.

The present invention provides methods for measuring heparanase activity and for testing an agent or agents to determine its potential to inhibit heparanase activity. The methods of the present invention are simple to carry out. They can also be conveniently implemented into robotic systems for high throughput screening (HTS).

The HS component of HSPG in vivo serves as a low affinity receptor for fibroblast growth factor (FGF) on the cell surface. Upon heparanase cleavage, the FGF/HS complex is released from the cell surface to stimulate cell proliferation. During angiogenesis, metastasis, and inflammation, elevated heparanase activity promotes FGF/HS complex release from cell surface, extracellular matrix and basement membrane. The present invention may utilize the physiological relevance of heparanase catalytic activity to cell surface FGF/heparanase substrate complex activity in screening agents for their potential to inhibit heparanase catalytic activity.

The present invention encompasses assays in which heparanase substrate is immobilized via a heparanase substrate binding protein.

The present invention involves interacting immobilized heparanase substrate binding protein with labeled heparanase substrate. Heparanase substrate binding protein is immobilized on a solid support. Upon interacting the immobilized heparanase substrate binding protein with labeled heparanase substrate, the labeled heparanase substrate binds to immobilized heparanase substrate binding protein, resulting in heparanase substrate binding protein-immobilized labeled heparanase substrate. The heparanase substrate binding protein-immobilized labeled heparanase substrate is incubated with a heparanase enzyme solution to allow heparanase to enzymatically cleave the labeled heparanase substrate. Cleaved fragments resulting from the enzyme digestion are released into solution. The enzyme digest solution is tested remote from the solid support, to measure label for determining heparanase catalytic activity. This heparanase incubation in the absence of a test agent serves to set the point of 100% heparanase catalytic activity, from which the percent inhibition of heparanase activity due to a test agent can be calculated.

In testing an agent for its potential to inhibit heparanase catalytic activity, the heparanase enzyme and the heparanase substrate binding protein-immobilized labeled heparanse substrate are incubated in the presence of the agent. The enzyme digest solution is tested remote from the solid support, to measure the label for determining whether or not the agent has the potential to inhibit heparanse. A percent inhibition of heparanse activity may be calculated for a given agent based on the set point of 100% heparanse catalytic activity.

Heparanase substrate binding protein may be any protein, peptide or fragment thereof that binds heparanase substrate. Examples include FGF, VEGF, and PDGF.

FGF may be naturally occurring or synthesized. FGF can be obtained inexpensively by cloning and expression, for example, as described (25).

Heparanase enzyme may be naturally occurring or synthesized. Heparanase can be obtained by cloning and expression, for example, as described in Example 2.

The labeled heparanse substrate contains a heparanase substrate and at least one label attached to the heparanase substrate, for detection. In the present invention, heparanase substrate refers to a substrate which is cleavable into degradation products by the enzyme heparanase, and which has the ability to bind FGF. The heparanase substrate may be selected from heparan sulfate (HS), heparan sulfate proteoglycans (HSPG) and heparan sulfate analogs. The heparanase sulfate analogs in accordance with the present invention are analogs which are cleaved by heparanase enzyme. Although heparin is generally regarded as a heparanase inhibitor, certain heparin species which behave as heparanase substrates (33) are also considered heparan sulfate analogs in accordance with the present invention. The structural characteristics of heparin needed for FGF binding, however, are indicated to be distinct from those sufficient for displacement of βFGF bound to HS on cell surfaces and ECM (33, 36). Thus, heparin species which do not displace βFGF in vivo would not have the same physiological relevance in an assay using immobilized FGF as heparan sulfate, for instance. References 33 and 36 are incorporated by reference to the extent of an indication of types of heparin species which behave as heparanase substrates.

The at least one label for the heparanase substrate may be selected from fluorescent, radioactive, chemiluminescent and chromogenic molecules. The heparanase substrate may be labeled with one or more labels. If desired, label(s) for the heparanase substrate can be selected for their ability to provide sensitive signal detection.

A fluorescent label refers to a fluorophore or a group containing a fluorophore. Because the fluorophore emits absorbed light at a characteristic wavelength, the fluorescently labeled heparanase substrate is detectable using known fluorescent detection means. The fluorescent label may be, for example, fluorescein (as, for example, fluorescein isothiocyanate (FITC or $F_2$FITC), lanthanide chelates, rhodamine, etc. Commercially available lanthanides are currently europium (Eu), samarium (Sm), terbium (Tb) and dysprosium (Dy).

Use of FITC as label allows for sensitive detection of fluorescence intensity and can advantageously be used for testing large numbers of agents. $F_2$FITC has slightly better photostability, fluorescence and requires less quenching than FITC. Eu-chelate, a lanthanide chelate, exhibits a long decay fluorescence. Assays using Eu-chelate can eliminate the contribution of any fluorescence detected due to the agent being tested.

Recently, time-resolved fluorometric (TRF) assays using Eu-chelates as fluorophores has been widely used for HTS (29, 30). These fluorophores exhibit an intense and long-lived fluorescence emission, making it possible to measure fluorescence after a delay time. This eliminates the background counts from short-lived fluorescent emissions from organic fluorophores that accompany the sample because they will have decayed prior to detection. This time-delayed fluorescence, in combination with a large stokes shift (340-625 nm), effectively reduces background emissions and contributes to assay sensitivity. Assays developed using Eu-labeled HS and Eu-labeled biotin-HS show higher sensitivity than those using FITC label. Eu(DPTA), DPTA being 1-(p-isothio-cyanatobenzyl) diethylenetriamine-N1,N1,N2, N3,N3-pentaacetic acid, is also sensitive, yet it is more stable than Eu-chelate at the acidic conditions of heparanase digestion (i.e., pH 5.4).

When a fluorescent label is used, the enzyme digest samples are passed through a light source, such as a laser emitting at the excitation wavelength of the fluorophore. Fluorescence is measured by reading the emitted photons at the emission wavelength of the fluorophore. For example, the excitation wavelength for fluorescence is about 494 nm and for Eu chelate it is about 340 nm. The emission wavelength for fluorescein, for example, is about 518 nm and about 615 for Eu-chelate.

An example of a radioactive label is tritium ($H^3$). An example of a chromogenic label is para-nitrophenyl (PNP).

The agent or agents screened for can be of any type. They can be naturally occurring or man-made (synthetic) agents. For example, the agents can be small molecular weight compounds, peptides, proteins or antibodies. It is known that catalytic activity of an enzyme can be inhibited by binding antibody to the active site. As used herein, the term "antibody" refers to any monoclonal or polyclonal immunoglobin, or fragment of an immunoglobin, e.g., Fab 1 or Fab 2. The immunoglobin may be a "humanized" antibody which comprises fused or grafted antibody regions wherein at least one of the regions is derived from a human antibody.

The heparanase substrate is immobilized to a solid support which is appropriate for in vitro testing purposes. Examples of a solid support include a microtiter plate, sepharase beads and polymer beads.

The method is sensitive. Only about 1 out of 10 potential cleavage sites on the labeled heparanase substrate are masked due to the binding with FGF.

The high throughput capability of the FGF/labeled heparanase substrate assay can be realized in adapting it to a robotics system. For example, a screening throughput of more than 25,000 compounds per day was achieved for the FGF/FITC-HS assay using a Zeiss uHTS system. To eliminate any positive results due to intrinsic fluorescence of test compounds, the FGF/EU-HS assay, for example, can be used to retest agents which tested positive in the FITC-HS/FGF assay.

In another aspect of the present invention, heparanase substrate is bound to at least one label and to an immobilization bridge. An immobilization bridge, in the present invention, is a group or groups (a) which is capable of binding to heparanase substrate, (b) which, when bound to labeled heparanase substrate (i) does not interfere with heparanase catalytic activity of the labeled heparanase substrate, and (ii) does not interfere with or add extraneous signals to measurement of the at least one label, and (c) which binds to a molecule capable of being immobilized to a solid support. The labeled heparanase substrate bound to an immobilization bridge is interacted with the immobilized molecule that specifically binds to the immobilization bridge. The resulting bridge-immobilized labeled heparanase substrate is then reacted with heparanase. The products of heparanase cleavage are released as labeled fragments in solution. The solution is measured for label remote from the solid support.

For example, the immobilization bridge and the corresponding molecule immobilized on a solid support may be biotin and streptavidin (SA) or avidin, respectively.

In an embodiment of the present invention, the heparanase substrate is HS, the label is a fluorescent label and the immobilization bridge and the corresponding molecule immobilized on a solid support are biotin and streptavidin, respectively. Biotin binds to the terminal sugar of the HS chain rather than heparanase cleavage sites. Thus, the binding of the fluorescently labeled biotin-HS to SA should not interfere with heparanase catalytic action.

In the alternative to the use of heparanase substrate being attached to at least one label and an immobilization bridge, heparanase substrate may be bound to an immobilization bridge without label. In this aspect of the invention, an assay testing an agent for its potential to inhibit catalytic activity using FGF-immobilized labeled heparanase substrate is performed as indicated previously. Also, an assay testing the agent using heparanase substrate bound to an immobilized bridge is performed. This assay using heparanase substrate bound to an immobilization bridge may be advantageously used to determine whether or not heparanase inhibitory activity for test agents that are found to inhibit heparanase activity in the FGF/labeled heparanse substrate assay is confirmed.

IC50 refers to the concentration of an agent required to inhibit 50% of a specific measured activity. In the present invention, the specific measured activity referred to is heparanase catalytic activity. An IC50 may be obtained for each test agent. Further information regarding the determination of IC50 can be found in Example 16.

Detecting the presence or absence of label in the enzyme digest solution is done at a location remote from the solid support. The measurement is performed at the remote location so that the label measurement is not skewed by label that may remain immobilized on the solid support. The location remote from the solid support need not be any particular distance away from the solid support. Measurement of label could take place in close proximity to the solid support, for instance, with the use of a shield to detection of label remaining on the solid support and be remote from the solid support in accordance with the present invention.

Agents that were determined to inhibit heparanase activity by the method of the FGF/labeled heparanase substrate assay were tested in kinetic assays as in Example 17. The results (not included here) indicated that these agents were competitive or mixed inhibitors of heparanase at the heparanase enzymatic active site. Examples 18-21 also provide validation of the FGF/labeled heparanase substrate assay.

The present invention also includes a method for screening agents to determine whether or not they interfere with HS/FGF interactions as they could release labeled heparanase substrate fragments even in the absence of heparanase. Moreover, such agents could be useful as therapeutic agents in the treatment of cancer and diseases caused by abnormal neovascularization. Binding of labeled heparanase substrate to FGF coated plates can be monitored (see FIGS. 3 and 11A). To FGF coated plates, labeled heparanase substrate is added in an amount capable of binding to the immobilized FGF. The supernatent is measured for label remote from the solid support, which should provide a measure of background. In testing an agent, the agent and labeled heparanase substrate are interacted in solution with the immobilized FGF. The supernatent is tested remote from the solid support to detect the presence or absence of label, to determine whether or not the agent has the ability to inhibit binding between fibroblast growth factor and heparanase substrate. Agents that have the ability to inhibit binding will have a higher measure of label in the supernatent as compared to the background measurement.

With regard to the following Examples, heparan sulfate from bovine kidney was obtained from Seikagaku Corp. Fluorescein-5-isothiocyanate (FITC "Isomer I") and Oregon Green 488 isothiocyanate ($F_2$FITC) was obtained from Molecular Probes. DELFIA Eu-DTPA-ITC chelate, Wash Concentrate, Enhancement Solution was from Perkin-Elmer Life Sciences. Biotin-LC-hydrizde was obtained from Pierce. N-acetylmannosamine was from Lancaster. Bovine serum albumin (BSA), Triton X 100 and Tween 20 were from Roche Molecular Biochemicals.

EXAMPLE 1

Cloning, Expression and Purification of FGF bFGF was cloned and expressed as described (25). *E. coli* cells expressing bFGF were suspended in lysis buffer (20 mM NaPO4, 5 mM EDTA, pH 7.0) at a ratio of 1 gm cells/5 ml lysis buffer. Protease inhibitor cocktail tablets (EDTA-free; Roche Molecular Biochemicals) and lysozyme (200 micrograms/ml) were added, and the suspension was stirred for 30 min. at 4 degrees C. The sample was sonicated, RNAase and DNAase (Roche Molecular Biochemicals) were added (1 microgram/ml), and the sample was incubated for an additional 30 min. After centrifugation of the sample at 20,000 xg for 20 min., the supernatant was filtered thru a 0.8 micron filter and loaded onto a SP Sepharose column equilibrated with 20 mM NaPO4, 100 mM NaCl, 5 mM EDTA, pH 7.0. After washing the column with equilibration buffer, bFGF was eluted from the column with 20 mM NaPO4, 600 mM NaCl, 5 mM EDTA, pH 7.0. The eluted fraction was concentrated and loaded onto a heparin Sepharose column that had been equilibrated with the SP Sepharose elution buffer. The bFGF was eluted with 20 mM NaPO4, 2M NaCl, 5 mM EDTA, pH 7.0. The purified bFGF was concentrated after the addition of 1 mM DTT to the sample. To induce oligomer formation, the concentrated bFGF was dialyzed for 72 hrs. at 4 degrees C. against multiple changes of dialysis buffer (50 mM NH4HCO3, 50 mM NaCl, pH 8.0).

EXAMPLE 2

Cloning, Expression and Purification of Heparanase

A full-length human heparanase cDNA clone was obtained from the ATCC. Using the published sequence in GenBank (Accession # AF152376), oligos were designed to PCR-amplify the open reading frame (ORF) consisting of 1632 bp, while at the same time (i) adding restriction sites for subcloning (5' KpnI-3' NotI), (ii) appending the ORF at the C-terminus with a 6 amino acid epitope tag ("EE-tag", NH2-EFMPME —COOH) preceded by a flexible 4 amino acid linker (SGSG) and followed by a single Ala residue preceding the STOP codon.

```
The forward primer was 5'
GGGTACCATGCTGCTGCGCTCGAAGCCTGCGCTGCCGCCGCCGCTGATGC
TG.

The reverse primer was 5'
ATAGTTTAGCGGCCGCTCACGCTTCCATCGGCATGAATTCACCAGAACCA
GAGATGCAAGCAGCAACTTTGGCATTTCTTATCACAAAAAAACTATATGA
G.
```

The amplicon was obtained using a proofreading polymerase and the ATCC-plasmid as template. The resulting amplicon was digested with KpnI and NotI and subcloned into the mammalian expression vector pEFBOS. The sequence of the cloned ORF was verified prior to cotransfection of CHO cells with the Heparanase expression construct and a NEO selection plasmid.

A dihydro foliate reductase defective-Chinese Hamster Cells (CHOdhfr-) was used as host for transfection. The cells ($2 \times 10^5$ cells/well) were grown on DMEM supplemented with 10% (v/v) FBS plus 100 μM Na-hypoxanthine and 16 μM thymidine (1 X HT) in a 6-well tissue culture plate. Transfection was carried out by the addition to the culture with 0.5 ug of plasmid DNA encoded with heparanase (pEF-BOS), neomycin resistant (pRSV-Neo) and hihydrofolate reductase (pSV-dhfr) genes in a ratio of 15:1:1, respectively, in the presence of 2 μl of FuGene6 reagent (Roche Molecular Biochemicals). After 72 hours of incubation in a 37° C.-CO2-incubator, the culture medium was replaced with HT minus DMEM supplemented with 10% dialyzed FBS. The transfected culture was further incubated for 4-8 weeks with medium change three times/week. Cells survived from the selective medium were then transferred to 150 mm dishes seeded with $1 \times 10^6$ cells/dish in HT minus DMEM containing 10% dialyzed FBS and increasing concentrations of methotrexate (MTX) from 0.1 to 3.0 μM. A clone designated as CHOB3 was selected from over 100 colonies that exhibited heparanase activity. The expression of heparanase by clone CHOB3 is about 4 fold higher than that of the untransfected CHO cells.

Production of heparanase with Clone CHOB3 was carried out by the following two methods:

a) Heparanase production in roller bottles: Corning 850 cm2 roller bottles were used. Each bottle was inoculated with $2.4\times10^7$ cells in 150 ml DMEM supplemented with 10% (v/v) dialized FBS plus 3 μM MTX and 25 mM of Hepes buffer. A 100-bottle batch was worked up by incubating the bottles for 5 to 7 days on a roller bottle rack rolling at a speed of 5 revolution/min. Cells pellets were collected from bottles after trypsinization by centrifugation after phosphate saline buffer washing.

b) Heparanase production in suspension culture: A 10-L bioreactor containing 7 L of Excel 301 medium (JRH) supplemented with 5% dialized FBS, 3 μM MTX, 0.1% pluronic acid and 25 mM Hepes was inoculated with CHOB3 culture to give an initial cell concentration of $5\times10^5$ cells/ml. The suspension culture was incubated at 35° C. for 4-5 days when cell density reached $3\times10^6$. Cells were harvested for isolation and purification of heparanase.

CHO cells expressing heparanase were suspended in Lysis Buffer (50 mM Tris, 150 mM NaCl, 0.5% Triton X-100, pH 7.5) at $2\times10^7$ cells/ml, protease inhibitor cocktail tablets were added (Roche Molecular Biochemicals), and the sample was sonicated briefly. The sample was then stirred at 4° C. for 30 min. followed by centrifugation at 100,000 xg for 60 min. The soluble fraction ("100 kxg-sup") was passed through 0.8 and 0.45 micron filters and used for enzymatic assays. To confirm that the activity observed in the "100 kxg-sup" was due to heparanase, a small amount of heparanase was purified by a method essentially as described (25).

EXAMPLE 3

Preparation of Fluorescein Labeled HS (FITC-HS or $F_2$FITC-HS)

HS was labeled with Oregon Green 488 isothiocyanate ($F_2$FITC) and other HS was labelled with fluorescein-5-isothiocyanate (FITC) by the procedure as described (25). Typically, HS from bovine kidney (60 mg) was dissolved in 16 ml of 0.1 M $Na_2CO_3$ (pH 9.35). FITC (94 mg) or $F_2$FITC (103 mg) in 0.8 ml of DMSO was added slowly (dropwise) to HS solution and stirred at 4° C. for 18 hrs in the dark. The reaction was stopped by 1 M Tris-HCl, pH 8.0 (0.5 ml) and the solution stirred at room temperature for 20 min. The sample was then applied to a Sephadex G-25 column (2.5×30 cm) in PBS to remove the excess FITC reagent. Fractions containing fluorescein labeled HS were pooled. Extent of fluorescein labeling was estimated by reading absorbance at 490 nm ($\epsilon=72,000$ $M^{-1}$). Typically, the molar ratio of fluorescein to HS was 0.6.

EXAMPLE 4

Preparation of Eu-Chelate-Labeled HS

HS (3.3 mg) was dissolved in 0.2 ml of 0.2 M $Na_2CO_3$ (pH 9.35). To the solution was added DELFIA Eu-DTPA-ITC chelate (1 mg in 0.1 ml $H_2O$) and stirred at room temperature for 1 hr followed by 14 hrs at 4° C. The sample was then loaded onto a Sephadex G-50 column (fine grade, 1.5 cm×50 cm) in TBS (50 mM Tris-HCl, pH 7.5, 100 mM NaCl). Before loading the sample, the column was loaded with 10 mg of BSA (to saturate nonspecific binding) and 20 ml of 20 mM EDTA followed by 60 ml of TBS. Fractions containing Eu-labeled HS were pooled. Extent of labeling was estimated by a standard curve of known concentrations of Eu-chelate solutions. Typically, the molar ratio of Eu-chelate to HS was 0.54.

EXAMPLE 5

Preparation of Biotin-HS (4.5 mg) was dissolved in 0.2 ml of $H_2O$ followed by 0.6 ml of methanol. To the solution was added 5.0 mg of solid biotin-LC hydrizide followed by 4 μL of 0.5 M $NaHCO_3$ in 10% methanol. The reaction was allowed to proceed at 50° C. for 1 day. $NaCNBH_3$ (25 mg) was then added to the solution. The solution was made clear by the addition of 0.2 ml of $H_2O$. The reaction incubated at 50° C. for 2 days. Two additional amounts (25 mg each) of $NaCNBH_3$ were added and reaction incubated at 50° C. for 2 days after each addition. The sample was then concentrated by speed-vacuum to 0.3 ml, diluted with $H_2O$ to 0.5 ml, and loaded onto a Sephadex G-25 column in PBS. Fractions containing HS were pooled and pH adjusted to 9.4 by the addition of 30 μl of 1 M of $Na_2CO_3$.

EXAMPLE 6

Preparation of Fluorescein Labeled Biotin-HS ($F_2$FITC-HS-Biotin)

$F_2$FITC (0.8 mg in 80 μl of DMSO) was added to the biotin-HS solution of Example 5 while stirring and reaction proceeded at 4° C. overnight in the dark. The sample was loaded onto a Sephadex G-25 column and eluted with PBS. Fractions containing $F_2$FITC labeled biotin-HS were pooled. Extent of fluorescein label was estimated by reading absorbance at 490 nm. The molar ratio of fluorescein to HS was 0.6.

EXAMPLE 7

Preparation of Eu-Chelate Labeled Biotin-HS (Eu-HS-Biotin)

To the biotin-HS solution (0.34 ml, 4.5 mg/ml in PBS) prepared as described in Example 5 was added 6.5 mg $Na_2CO_3$ to adjust the pH to 9.4. Eu-DTPA-ITC chelate (1 mg) was dissolved in 0.1 ml of 10 mM sodium acetate (pH 4.8) and 50 μl of this solution was added to the biotin-HS solution while stirring. The reaction was shaken for 1 hr at 25° C. followed by 15 hrs at 4° C. and further 4 hrs at 25° C. The sample was then loaded onto a Sephadex G-50 column (fine grade, 1.5 cm×50 cm) in TBS. Before loading the sample, the column was loaded with 10 mg of BSA (to saturate nonspecific binding) and 20 ml of 20 mM EDTA followed by 60 ml of TBS. Fractions containing Eu-labeled HS were pooled. Extent of labeling was estimated by a standard curve of known concentrations of Eu-chelate solutions. The molar ratio of Eu-chelate to HS was 0.34.

EXAMPLE 8

Preparation of $^3$H Labeled HS $^3$H labeled HS was prepared as described previously (26). Typically, HS (10 mg) was dissolved in 0.38 ml of hydrazine hydrate containing 7.6 mg of hydrazine sulphate and the mixture heated at 100° C. for 2 h in a capped glass vial. The mixture was cooled and dried under argon. Toluene (0.4 ml) was added and the mixture dried by rotary vac-evaporation. This procedure was repeated twice. The residue was dissolved in 0.9 ml of 1M NaCl and desalted on a Sephadex G-25 column in water. Desalted material was loaded onto a Dowex 50 (X-8, $Na^{+1}$ form) column (1.0 cm×3.0 cm) and washed with 5 ml of water. "Flow through" and "Wash" fractions were pooled and lyophilized. The resulting N-deacetylated HS was dissolved in 0.5 ml of 0.5 M $NaHCO_3$ containing 10%

(V/V) methanol, cooled to 0° C. in an ice bath and 30 µl of [³H]acetic anhydride (3 mCi, 500 mCi/mmole) in toluene added. The mixture was stirred vigorously at 0° C. for 3 hr. An additional 0.5 ml of 0.5 M $Na_2CO_3$, 20 µl of MeOH and 25 µl of acetic anhydride were added with stirring for 30 min at 0° C. This procedure was repeated once more. After the mixture was warmed up to room temperature, the toluene was removed under a stream of argon and the solution desalted on a Sephadex G-25 column in 20 mM ammonium acetate, pH 6.8. [³H] labeled HS was pooled and aliquots stored at −20° C.

EXAMPLE 9

Heparanase Assay Using FITC-HS or $F_2$FITC-HS and FGF Coated Plates (FITC-HS/FGF Assay)

FGF (1.97 mg/ml) was diluted with PBS to 18.75 µg/ml and coated onto 384 well solid black High Binding plates from Costar (40 µl/well) at 4° C., overnight. Plates were blocked with 1% BSA/PBS (60 µl/well) at 37° C. for 1 hr and washed with PBS/0.02% Tween 20 (60 µl/well, 4 times). FITC-HS or $F_2$FITC-HS (0.15 µg/well/40 µl in PBS, 1% BSA, 0.02% Tween 20) was added and incubated at 37° C. for 1-1.5 hr. Plates were washed with PBS/0.02% Tween 20 (60 µl/well, three times). Crude heparanase from transfected CHO cells (1 µl of "100 kxg-sup" of Example 2 containing 5 µg of total protein in Lysis Buffer) and purified heparanse (20 ng) were each diluted with 40 µl of Assay Buffer (50 mM sodium acetate, pH 5.0, 0.2 mg/ml BSA, 5 mM N-acetyl-mannosamine, 0.05% Triton X 100), added into each well, and incubated at 37° C. for 30 min. Enzyme reaction was stopped by the addition of 5 µl/well of 1 M Tris-HCl, pH 8.0. Solution (35 µl/well) was then transferred to a microtiter plate for fluorescence reading (excitation at 485 nm and emission at 535 nm) on a Victor 2 reader (Perkin Elmer Life Sciences).

EXAMPLE 10

High Throughput Screening (HTS) Heparanase Assay Using FITC-HS on FGF Coated Plates HTS FITC-HS/FGF heparanase assay was implemented into a Zeiss uHTS system, which consists of one 384 well pipetor, three 96 well pipetors, two washers, two Multidrop dispensers, four Cybidrop dispensers, three incubators and two Zeiss HTS readers. Microtiter plates (384 well) were coated with FGF, blocked with BSA and stored at 4° C. for up to 3 weeks. The plates were washed with PBS/0.02% Tween 20 followed by incubating with FITC-HS. For heparanase digestion, crude enzyme from the "100 kxg-sup" (1 µl/well) of Example 2 was used. All the steps for plate movements, liquid transferring, and fluorescence measurements were performed by robots.

Figure 9:
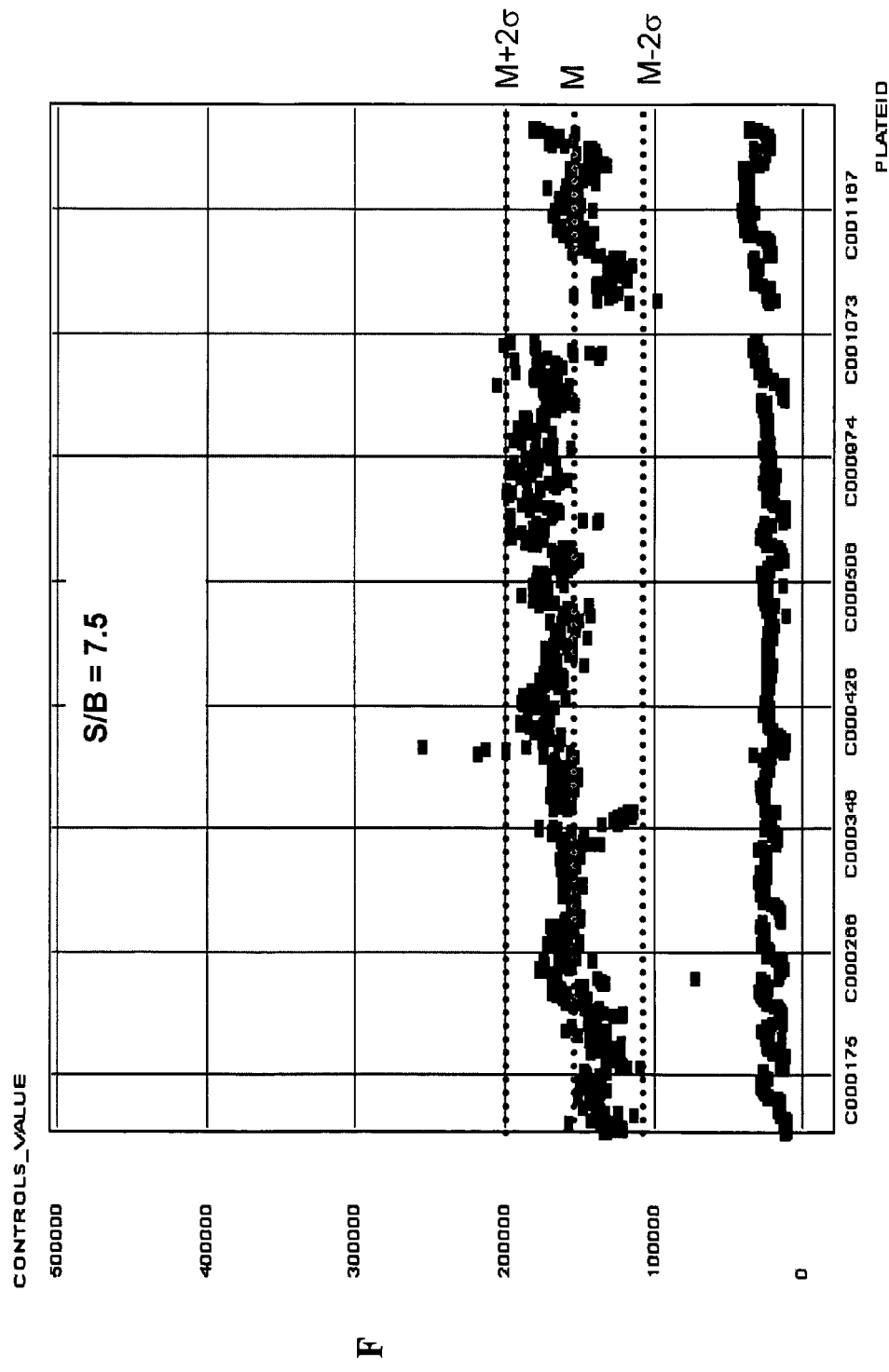
FIG. 9, a scatter plot of plate identification vs. fluorescence units (FU) in the $F_2$FITC-HS/FGF assay, shows total heparanase activity signal, i.e., average fluorescence intensity of the digest after addition of heparanase without any potential inhibitor, and shows background signal, i.e., average fluorescence intensity of assay buffer.
Figure 10:
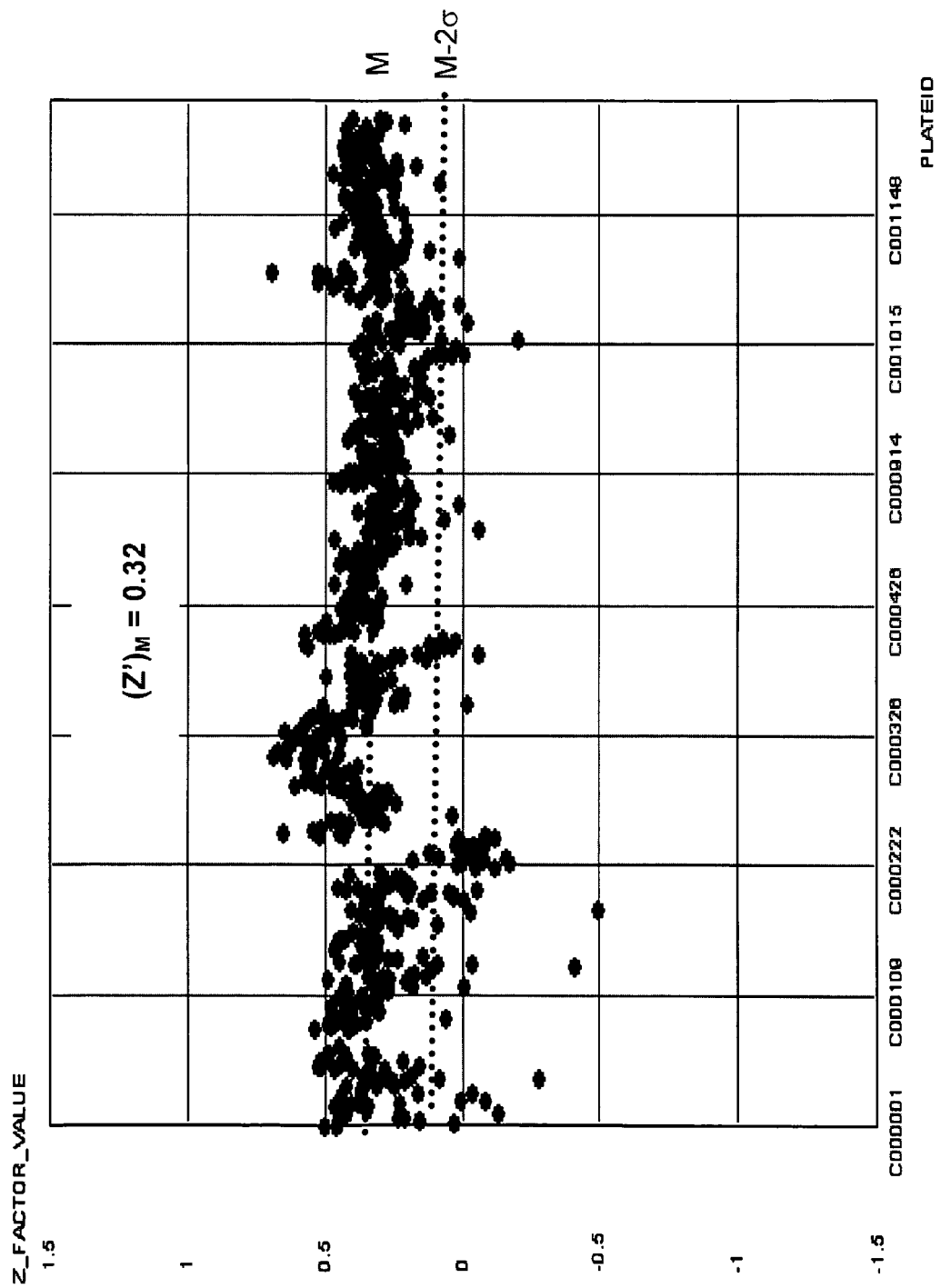
FIG. 10 is a scatter plot showing calculated Z' factors for plates indicated.

The overall signal to background ratio was 7.5 (FIG. 9) and the average Z' factor was 0.32 (FIG. 10). Agents having the potential to inhibit heparanase catalytic activity which inhibit greater than 65% of activity at a concentration of 25 µM were identified. Because some of these potential inhibitors were fluorescent agents, they were also tested in the Eu-HS/FGF assay (Example 11) on Zeiss uHTS and agents which tested positively were confirmed to be heparanase inhibitors.

EXAMPLE 11

Heparanase Assay Using Eu(DTPA) Labeled HS on FGF Coated Plates (Eu-HS/FGF Assay)

FGF was coated onto 384 well microtiter plates as in Example 9. Plates were blocked with 1% BSA/PBS (50 µl/well) at 37° C. for 1 hr and washed with TBS (60 µl/well, three times). Eu-labeled HS (40 µl/well, 0.375 µg/ml in TBS, 0.5% BSA, 0.02% Tween 20) was added to the plates and incubated at 37° C. for 1 hr. Plates were then washed with TBS (60 µl/well, three times). Crude heparanase (1 µl of "100 kxg-sup" of Example 2 containing 5 µg of total protein in Lysis Buffer) or purified heparanase (20 ng) was diluted with 40 µl of Assay Buffer (50 mM sodium acetate, pH 5.4, 0.2 mg/ml BSA, 5 mM N-acetylmannosamine, 0.025% Triton X 100), added into each well, and incubated at 37° C. for 30 min. Reaction was stopped by the addition of 1.0 M Tris-HCl, pH 8.0 (5 µl/well). Solution (8 µl/well) was transferred to a microtiter plate and mixed with 60 µl/well of Enhancement Solution at room temperature for 30 min. Signal was quantitated by reading time resolved fluorescence (TRF) at the wavelengths of EX(340 nm)/EM(615 nm) on a Wallace Victor 2 reader.

EXAMPLE 12

HTS Heparanase Assay Using Eu-HS on FGF Coated Plates

Heparanase assay using Eu-HS as a substrate was implemented into a Zeiss uHTS system. Plate movement and liquid transfer were performed by robotics. TRF measurement was done offline on a Victor 2 reader.

EXAMPLE 13

Heparanase Assay Using FITC-HS-Biotin (or $F_2$FITC-HS-Biotin) on Streptavidin (SA) Coated Plates (FITC-HS-Biotin/SA Assay)

Figure 12A:
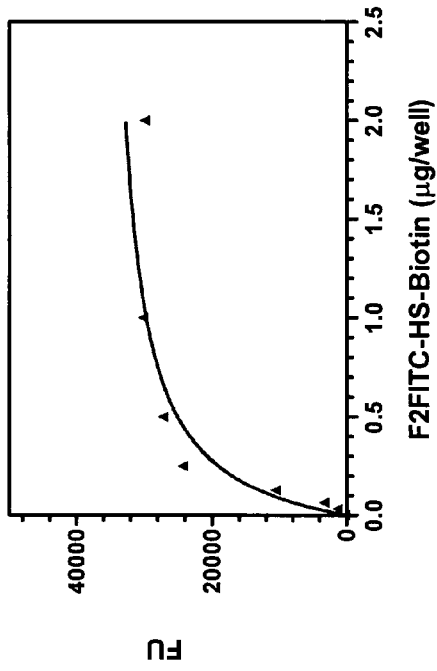
FIG. 12A graphically shows $F_2$FITC-HS-biotin concentration dependent binding to SA coated plates.
Figure 12B:
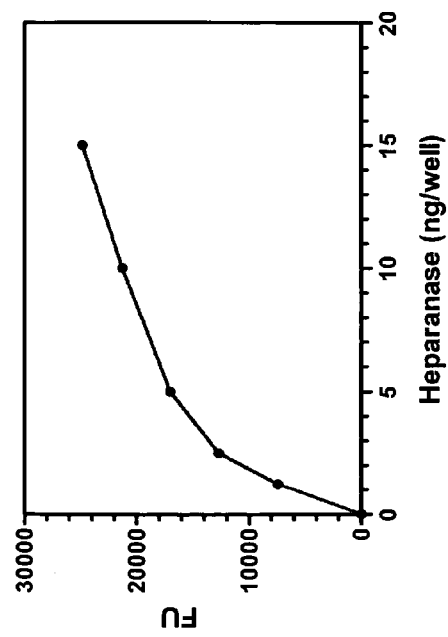
FIG. 12B graphically shows heparanase concentration dependent digestion of $F_2$FITC-HS-biotin on SA coated plates.

To prepare FITC-HS-biotin, HS was first treated with biotin-LC-hydrazide to attach the biotin group to the terminal sugar of HS. The resulting imine was then reduced to amine by $NaCNBH_3$. The labeled material (Biotin-HS) was then purified by passing through a gel filtration column and labeled with FITC as described in "Methods". FIG. 12A shows a concentration dependent binding of $F_2$FITC-HS-biotin to SA coated plates. The binding reached a plateau when 1 µg/well of $F_2$FITC-HS biotin was used. For the heparanase assay, 0.5 µg/well of $F_2$FITC-HS-biotin was used. A heparanase concentration dependent digestion of bound $F_2$FITC-HS on SA coated plates is shown in FIG. 12B.

Streptavidin (10 µg/ml in PBS, 40 µl/well) was coated onto 384 well solid black Enhancement Surface microtiter plates (Becton Dickinson) at 4° C. overnight. Plates were blocked with 1% BSA in PBS (40 µl/well) at 37° C. 1 hr (or 4° C. overnight) and washed with TBS (50 µl/well, three times). $F_2$FITC-HS-biotin (40 µl/well, 12.5 µg/ml) in 1% BSA, TBS was added to the plates and incubated at 37° C. for 1 hr. Plates were washed with TBS. Because biotin/SA interaction is extremely tight (Kd=$10^{-16}$ M), very few agents (e.g. biotin-like agents) would be able to block the interaction. Crude heparanase (1 µl of "100 kxg-sup" containing 5 µg of total protein in Lysis Buffer) or purified heparanase (20 ng) was diluted with 40 µl of Assay Buffer (50 mM sodium acetate, pH 5.4, 0.2 mg/ml BSA, 5 mM N-acetylmannosamine), added into each well, and incubated at 37° C. for 25 min. One molar Tris-HCl, pH 8.0 (5 µl/well) was added and 35 µl/well of solution was transferred to a microtiter plate for fluorescence measurement (excitation at 470 nm and emission at 535 nm).

EXAMPLE 14

Heparanase Assay Using Eu-HS-Biotin on SA Coated Plates (Eu-HS-Biotin/SA Assay)

Figure 13A:
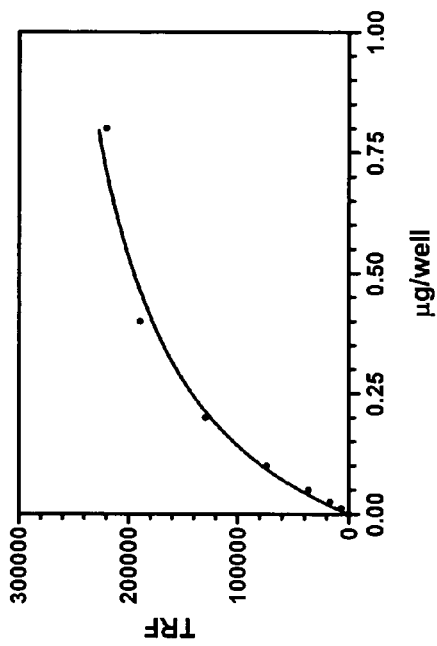
FIG. 13A graphically shows Eu-HS-biotin concentration dependent binding to SA coated plates in a plot of concentration vs. measured TRF.
Figure 13B:
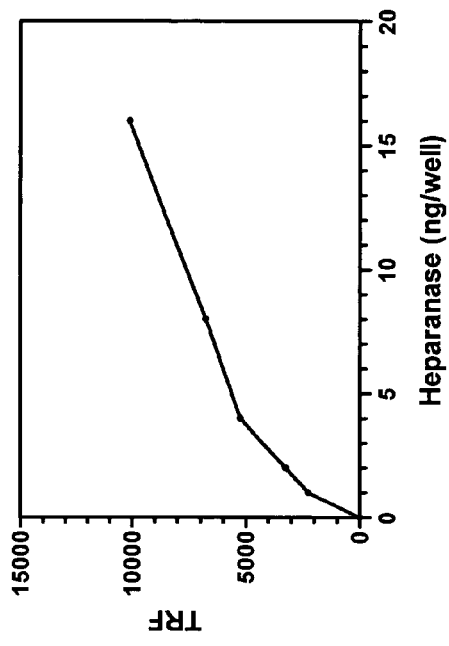
FIG. 13B graphically shows heparanase concentration dependent digestion of Eu-HS-biotin on SA coated plates in a plot of concentration vs. measured TRF.

Biotin-HS was labeled with Eu(DTPA)ITC. Binding of Eu-HS-biotin to SA coated plates is shown in FIG. 13A, which is similar to that of $F_2$FITC-HS-biotin. A heparanase concentration dependent digestion is also similar to that of $F_2$FITC-HS-biotin (FIG. 13B).

Plates were coated with streptavidin and blocked with BSA as described above. Eu-HS-biotin (40 µl/well, 7.5 ug/ml) in 1% BSA, TBS was added to the plates and incubated at 37° C. for 1 hr. Plates were washed with TBS. Crude heparanase (1 µl of "100 kxg-sup" of Example 2 containing 5 µg of total protein in Lysis Buffer) or purified heparanase (20 ng) was diluted with 40 µl of Assay Buffer (50 mM sodium acetate, pH 5.4, 0.2 mg/ml BSA, 5 mM N-acetylmannosamine), added into each well, and incubated at 37° C. for 25 min. One molar Tris-HCl, pH 8.0 (5 µl/well) was added and 8 µl/well of solution was transferred to a microtiter plate that contains 60 µl/well of "Enhancement Solution". Time-resolved fluorescence was measured by a Victor 2 Reader.

Agents that were identified from the Eu-HS/FGF screening assays as having potential to inhibit heparanase were tested in this assay (Eu-HS-biotin/SA). The results indicated that IC50s were similar in both assays (data not shown).

EXAMPLE 15

TRF Heparanase Assay Using Eu-HS as a Substrate on FGF Coated Plates

Figure 11A:
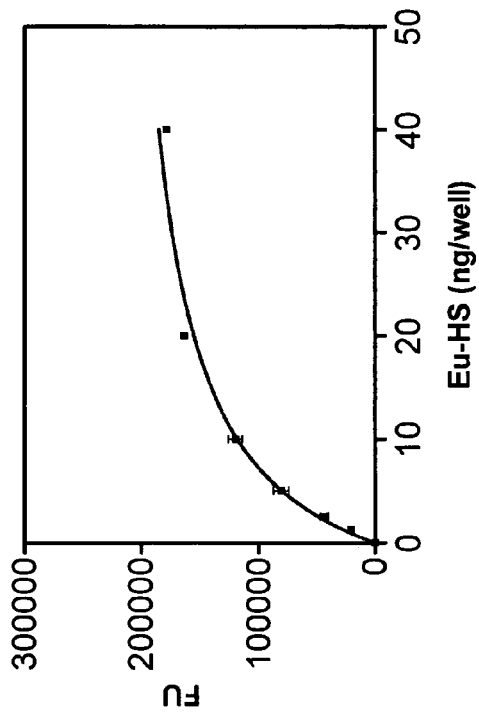
FIG. 11A graphically shows EU-HS concentration dependent binding to FGF coated plates.
Figure 11B:
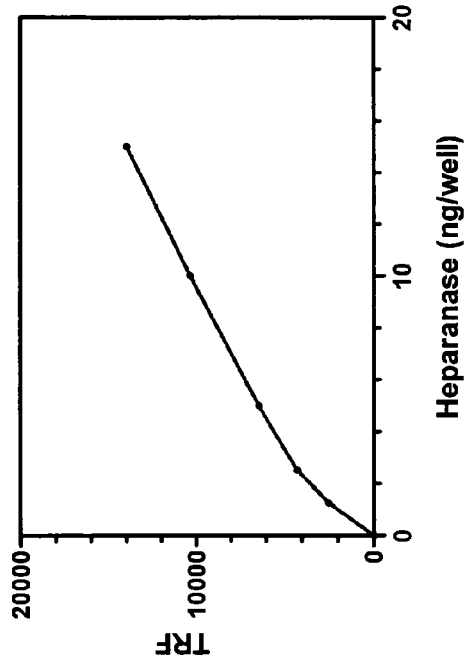
FIG. 11B, a plot of heparanase concentration vs. time-resolved fluorometric units (TRF), shows heparanase concentration dependent digestion of Eu-HS on FGF coated plates.

To develop a TRF assay for heparanase, HS was labeled with Eu-chelate (DTPA) ITC. FIG. 11A shows a concentration dependent binding of Eu-HS to FGF coated plates. The binding reaches plateau at 20 ng/well of Eu-HS. Eu-HS (15 ng/well) was incubated with FGF coated plates and washed extensively with TBS, bound Eu-HS was digested with heparanase. FIG. 11B shows a time dependent digestion of Eu-HS by purified heparanase. After 30 min, the signal to background ratio reached 8.0.

EXAMPLE 16

IC50 Determination

For IC50 determination of agents tested for heparanase inhibitory activity, agents were dissolved in DMSO at a concentration of 10 mM. An aliquot (4 µl) was further diluted with DMSO (16 µl) to a concentration of 2 mM. A series of 1:3 dilutions in DMSO were performed to achieve a concentration range of 0.1 µM-2 mM. Each sample was further diluted 25-fold with Assay Buffer. Aliquots (30 µL/well) were then added to assay plates containing immobilized substrates. An aliquot (20 ng/10 µl/well) of purified heparanase was then added, and plates were incubated at 37° C. for 20-30 min. Reactions were stopped by the addition of 1.0 M Tris-HCl, pH 8.0 (5 µl/well). Signals were quantitated by reading either fluorescence or TRF on a Victor 2 reader. Percent inhibition of heparanase catalytic activity by an agent at various concentrations was calculated by the following formula:

% inhibition=$100*[1-(F_s-F_b)/(F_t-F_b)]$, where $F_s$ is the fluorescence signal of the sample which included the agent, $F_b$ is the fluorescence signal in the absence of heparanase and agent, $F_t$ is the fluorescence signal in the presence of heparanase, but no agent.

EXAMPLE 17

Kinetic Analysis

Mechanistic analysis of agents determined to inhibit heparanase activity in FGF/labeled heparanase substrate of the present invention was carried out by measuring heparanase activity at various concentrations of labeled HS in the presence of the agents. Typically, various concentrations of labeled HS were immobilized onto assay plates. Heparanase solutions (with and without agents) were then added into wells (40 µl/well) containing various concentrations of immobilized labeled HS and incubated at 37° C. for 25 min. Reactions were stopped by the addition of 1.0 M Tris-HCl, pH 8.0 (5 µl/well) and label was measured remotely. Heparanase activities of reaction solutions containing no agent and heparanase inhibitory activities of the agents were then quantitated.

Heparanase activities without an inhibitory agent and with various concentrations of an inhibitory agent were analyzed by double reciprocol plots of 1/v versus 1/s, where v is the reaction rate and s is the substrate concentration. Inhibition mechanism (competitive, noncompetitive, uncompetitive or mixed) of an inhibitory agent was then determined by the slopes and intercepts (x- and y-axis) of the curves exhibited at various inhibitory concentrations.

EXAMPLE 18

$F_2$FITC-HS (or FITC-HS) as a Substrate for Heparanase

Figure 1B:
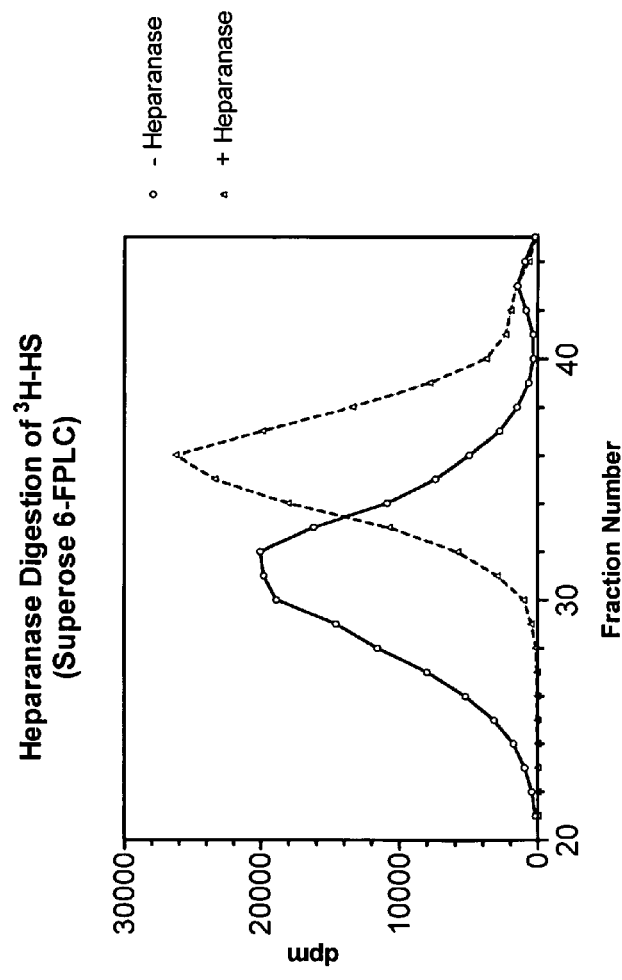
FIG. 1B graphically shows the products of heparanase digestion of $^3$H-HS eluted from a Superose 6-FPLC.

In the Heparanase assay using $F_2$FITC-HS (or FITC-HS) as a substrate on FGF coated plates (Example 9), the digested products were analyzed by gel filtration FPLC analysis. Toyoshima reported that FITC-HS is a substrate when the molar ratio of FITC to HS was less than 1.0 (26). HS was labeled with $F_2$FITC with a molar ratio of 0.6. (The molar ratio of FITC would be the same.) To confirm that it is a heparanase substrate, the digested products were analyzed by gel filtration (Superose 6)-FPLC (FIG. 1A). For comparison, [$^3$H] HS as substrate was also digested with heparanase and the products analyzed by FPLC (FIG. 1B). In both cases, the digested products eluted in similar positions, indicating that both FITC-HS and [$^3$H] HS are substrates for heparanase.

EXAMPLE 19

Figure 2:
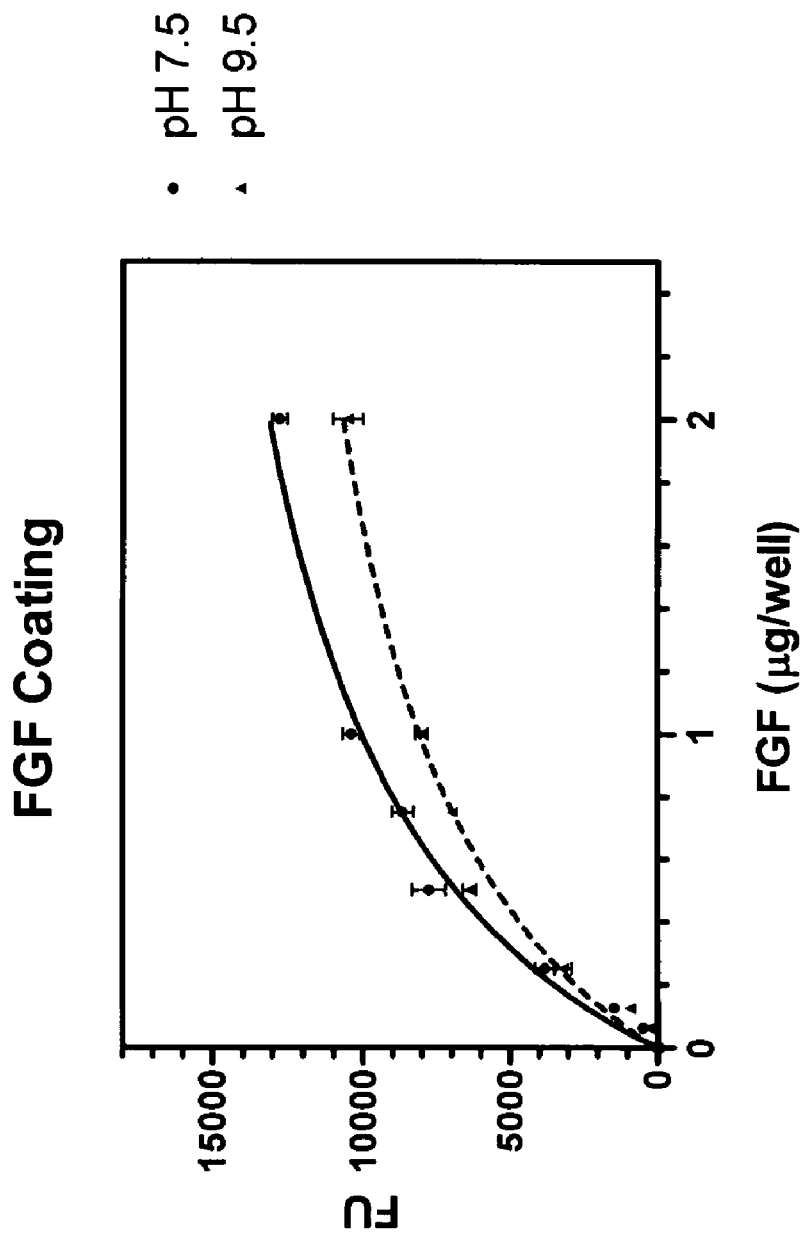
FIG. 2 graphically shows FGF concentration dependent binding to microtiter plates at pH 7.5 and pH 9.5.
Figure 3:
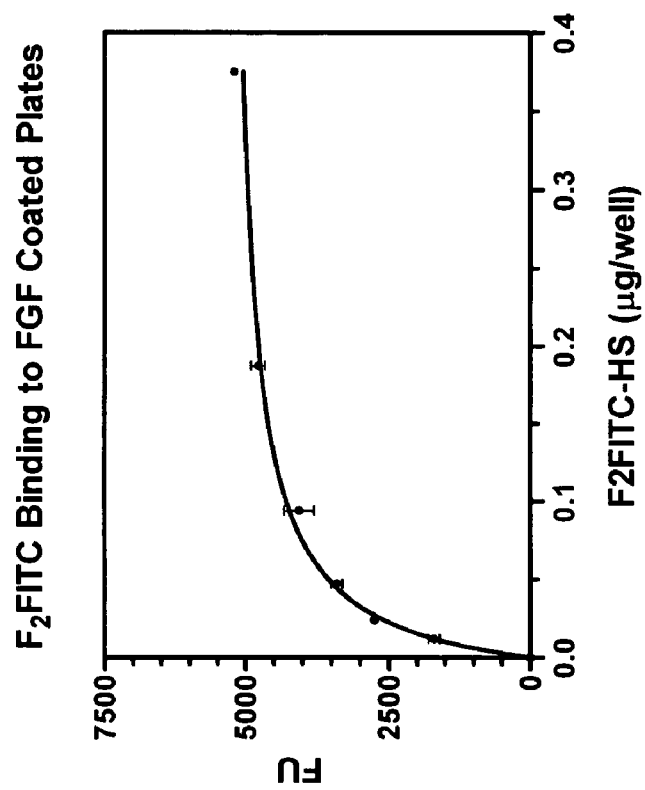
FIG. 3 graphically shows $F_2$FITC-HS concentration dependent binding to FGF coated plates.

Binding of $F_2$FITC-HS to FGF Coated Plates $F_2$FITC-HS binding to various concentrations of FGF (oligomer form) coated on the 384 well microtiter plates was studied. FIG. 2 shows that the binding reached a plateau when FGF concentration of 18.75 µg/ml (or 0.75 µg/40 µl/well) was coated on the plates. The results also showed that $F_2$FITC-HS binding was higher when FGF was coated at pH 7.5, instead of pH 9.5. When the same experiment was carried out using monomeric FGF (The form that is reduced by DTT), the binding was lower (data not shown). It is not clear whether the lower binding observed was due to a low coating efficiency or a low binding affinity of monomeric FGF (MW, ~16 k). $F_2$FITC-HS binding was found to be higher when FGF was coated onto Costar "High Binding" plates than that of "Regular" plates (data not shown). FIG. 3 shows a concentration depending binding of $F_2$FITC-HS to FGF coated at the concentration of 18.75 µg/ml. The binding reached a plateau when 0.1-0.2 µg/well of $F_2$FITC-HS was used.

EXAMPLE 20

Figure 4:
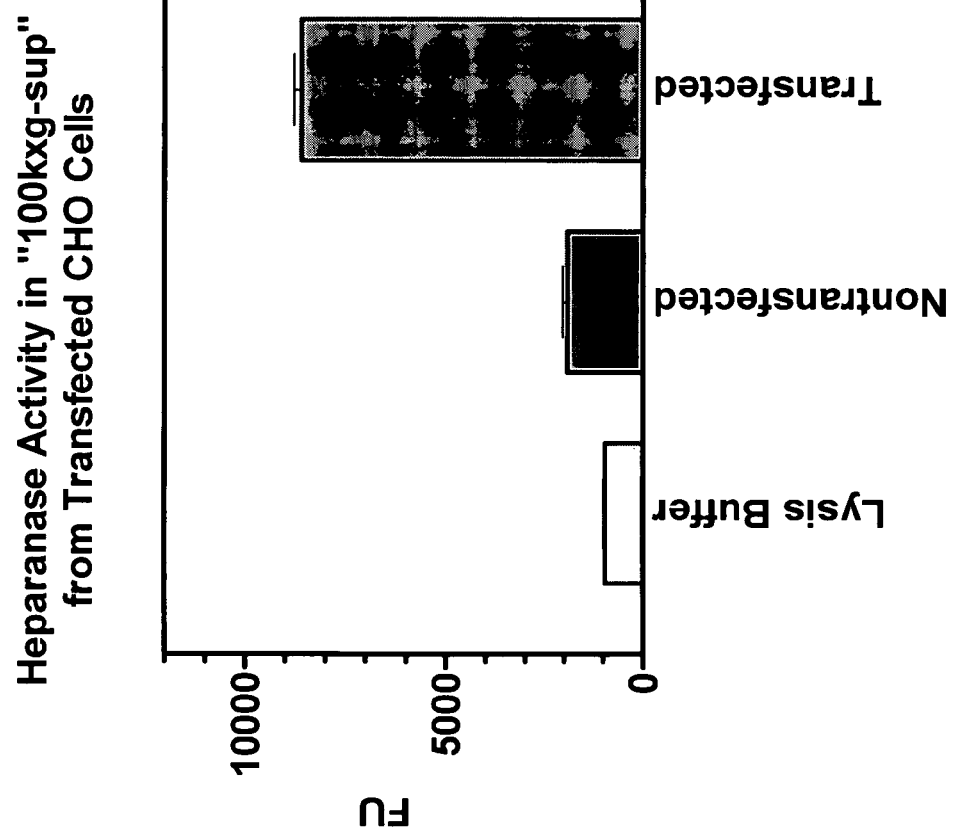
FIG. 4 graphically shows heparanase activity from the expressed product of transfected CHO cells.
Figure 5:
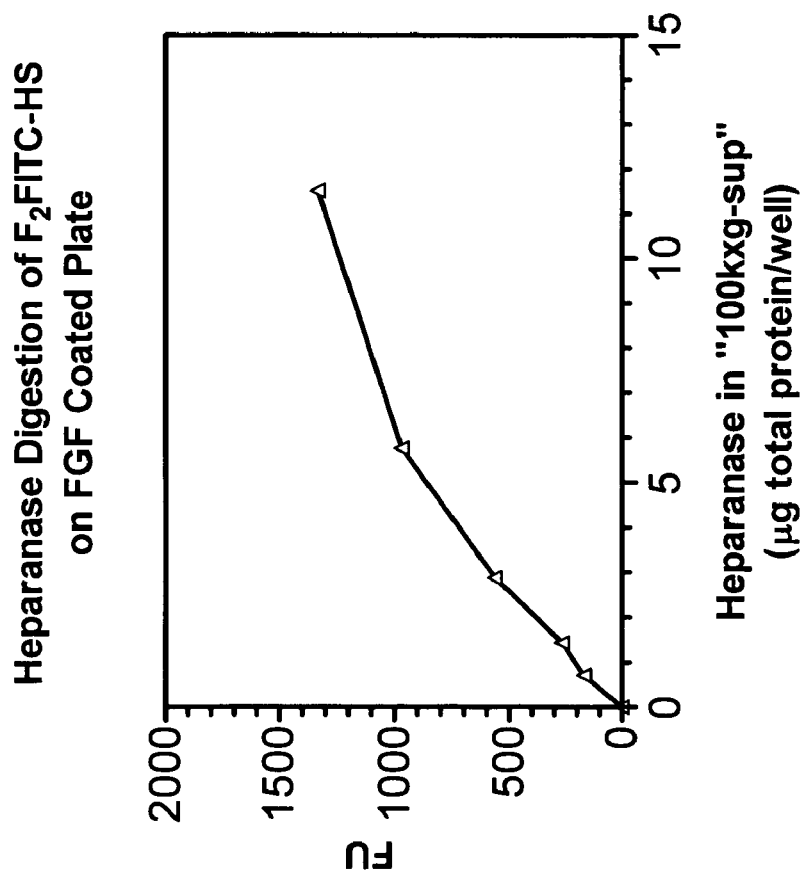
FIG. 5 graphically shows heparanase concentration dependent digestion of $F_2$FITC-HS on FGF coated plates.

Heparanase Digestion of $F_2$FITC-HS on FGF Coated Plates $F_2$FITC-HS was bound to FGF coated plates and digested with the "100 kxg-sup" from transfected CHO cells (Example 2). As shown in FIG. 4, fluorescence intensity in the medium increased as compared with lysis buffer, indicating that $F_2$FITC-HS fragments were released in the medium upon heparanase digestion. As a control, when bound $F_2$FITC-HS was incubated with the "100 kxg-sup" from non-transfected cells, no significant increase of fluorescence was observed. A heparanase concentration dependent digestion of $F_2$FITC-HS is shown in FIG. 5. Fluorescence intensity released in the medium was proportionally increased when increasing amounts of heparanase were used.

EXAMPLE 21

Measured Fluorescence Intensity Due to Heparanase Digestion of $F_2$FITC-HS

Figure 6:
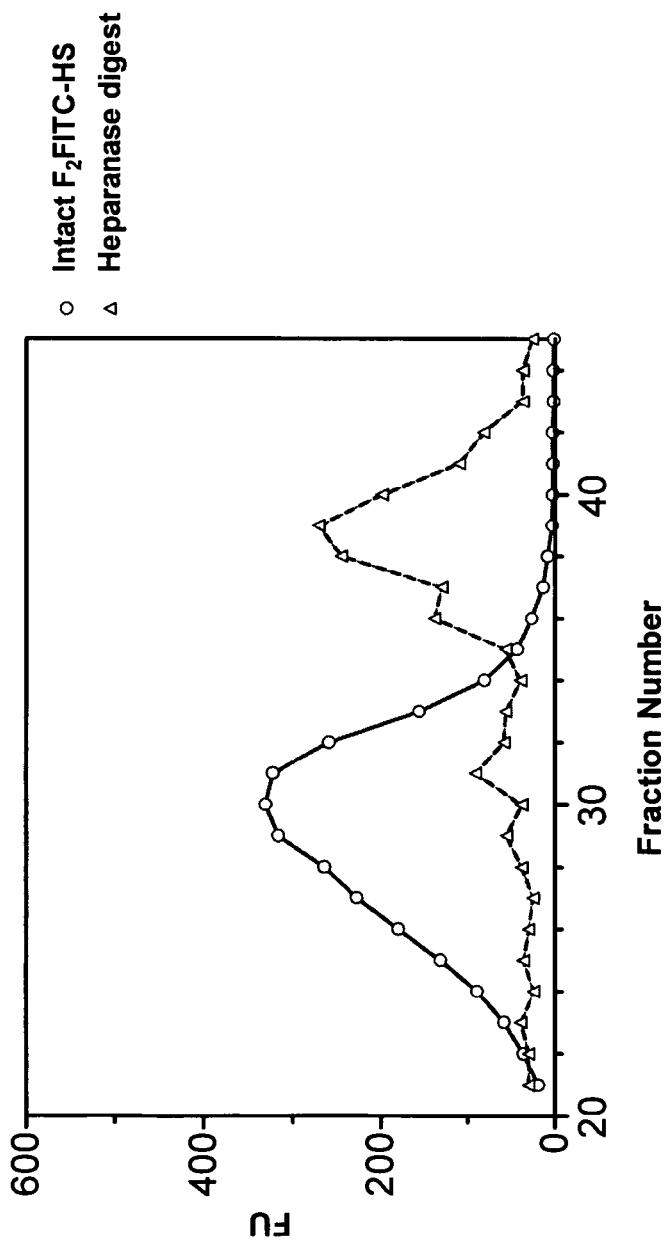
FIG. 6 graphically shows a Superose 6-FPLC elution of the heparanase digest from the $F_2$FITC-HS/FGF heparanase assay.
Figure 7:
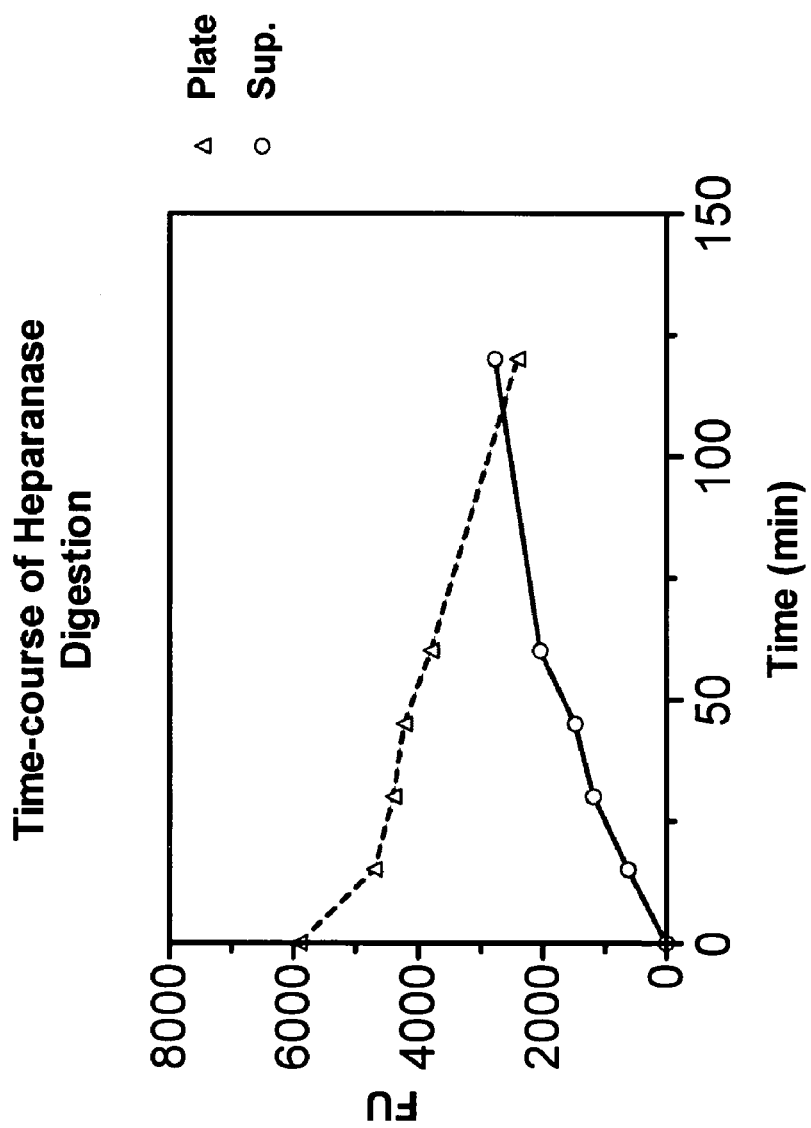
FIG. 7 graphically shows the time course of heparanase digestion.

To confirm that fluorescence intensity observed in the medium was due to heparanase digestion of $F_2$FITC-HS, four sets of experiments were performed. First, upon heparanase digestion, the cleaved products in the medium were analyzed by Superose 6-FPLC (FIG. 6). Fluorescent material was eluted slower than that of intact $F_2$FITC-HS, indicating that they are $F_2$FITC-HS fragments generated by heparanase reaction. Second, a time dependent heparanase digestion of $F_2$FITC-HS was carried out. The extent of hydrolysis was monitored by the release of digested fragments in the medium and the undigested material remained on the plate. As is shown in FIG. 7, fluorescence intensity in the supernatant increased upon digestion, whereas fluorescence intensity associated with the plate decreased, indicating that intact $F_2$FITC-HS was degraded and released in the medium. Third, heparanase activity was measured in the "100 kxg-sup" at different pHs and found that the optimal pH for the activity was 5.1 (FIG. 8), consistent with that reported by the literature (26, 28). Fourth, $F_2$FITC-HS was digested with purified heparanase. A concentration dependent digestion curve similar to that shown in FIG. 4 was also observed (data not shown).

Further information regarding the Figures is as follows:

FIG. 1 Analysis of Heparanase Digested Products by Superose 6-FPLC.

(A) $F_2$FITC-HS (20 µl, 1.9 mg/ml) was diluted with 80 µl of 50 mM sodium acetate, pH 5.0, 0.1 mg/ml BSA and 5 mM N-acetylmannosamine. An aliquot (20 µl) was digested with heparanase expressed by transfected CHO cells, i.e., "100 kxg-sup" (5 µl in Lysis Buffer as described in "Methods") at 37° C. for 20 hrs. The sample was then diluted with PBS and loaded onto Superose 6-FPLC in PBS with a flow rate of 0.25 ml/min. Collected 0.5 ml/fraction. An aliquot (25 µl) in each fraction was withdrawn and transferred to a 384 well microtiter plate for fluorescence counting.

(B) $^3$H labeled HS (20 µl, 2.6 mg/ml) was diluted with the buffer as described in (A). An aliquot (20 µl) was digested with heparanase and the products were analyzed by Superose 6-FPLC as described in (A). Radioactivity in each fraction was measured by a scintillation counter.

FIG. 2 FGF Concentration Dependent Coating at 2 Different pHs.

FGF (1.81 mg/ml) was diluted with either PBS (pH 7.5) or 50 mM $Na_2CO_3$ and 100 mM NaCl (pH 9.5) to various concentrations (2.5 µg/ml-50 µg/ml). Aliquots (40 µl/well) were coated onto 384 well microtiter plates (black solid "High Binding" plates from Costar) at 4° C., overnight. Plates were blocked with 1% BSA in PBS at 37° C., 1 hr and washed with PBS. $F_2$FITC-HS (1.5 µg/well/40 µl in PBS, 1% BSA, 0.02% Tween 20) was added and incubated at 37° C. for 1 hr. Plates were washed with PBS/0.02% Tween 20. Bound material was then eluted from plates with 0.1% SDS in PBS and quantified by fluorescence intensity. FU is a fluorescence unit measured by Victor 2 reader.

FIG. 3 $F_2$FITC-HS Concentration Dependent Binding to FGF Coated Plates.

FGF (18.75 µg/ml in PBS) was coated onto 384 well plates (40 µl/well) at 4° C., overnight and blocked with 1% BSA/PBS. Various amounts (0.012-0.375 µg/40 µl/well) of $F_2$FITC-HS in PBS, 1% BSA, 0.02% Tween 20 were added and incubated at 37° C. for 1 hr. Plates were washed with PBS/0.02% Tween 20. Bound material was eluted with 0.1% SDS in PBS and quantified by measuring fluorescence.

FIG. 4 Heparanase Activity from Expressed Product of Transfected CHO Cells

FGF was coated onto microtiter plates and incubated with $F_2$FITC-HS as described. Bound $F_2$FITC-HS was treated with the "100 kxg-sup" sample from transfected or nontransfected CHO cells (1 µl sample in Lysis Buffer diluted with 40 µl of Assay Buffer in each well) at 37° C. for 30 min. As a control, bound $F_2$FITC-HS was also treated with the Lysis Buffer (1 µl Lysis Buffer diluted with 40 µl of Assay Buffer in each well). Reactions were stopped by 1.0 M Tris-HCl, pH 8.0 (5 µl/well). Aliquots (35 µl/well) were withdrawn for fluorescence reading.

FIG. 5 Heparanase Concentration Dependent Digestion of $F_2$FITC-HS on FGF Coated Plates.

$F_2$FITC-HS/FGF assay was carried out as described except that various amounts of heparanase in "100 kxg-sup" from transfected CHO cells were used.

FIG. 6 Superose 6-FPLC Analysis of Digested Products in $F_2$FITC-HS/FGF Assay.

$F_2$FITC-HS/FGF assay using crude heparanase was carried out as described. After digestion, reaction mixture in the medium (140 µl combined from 4 wells) were loaded onto Superose 6-FPLC in PBS. Fractions were collected and fluorescence intensity in each fraction was counted as described in FIG. 1. As a control, intact $F_2$FITC-HS was also loaded onto Superose 6-FPLC and analyzed.

FIG. 7 Time-Course of Heparanase Digestion.

$F_2$FITC-HS/FGF assay using crude heparanase was carried out as described. At various time points of digestion, 1.0 M Tris-HCl was added into wells (5 µl/well) to stop reactions. Supernatant was withdrawn for analyzing cleaved $F_2$FITC-HS fragments by fluorescence measurement (o). Undigested $F_2$FITC-HS remaining on the plates was extracted by 0.1% SDS in PBS and analyzed by fluorescence measurement (Δ).

Figure 8:
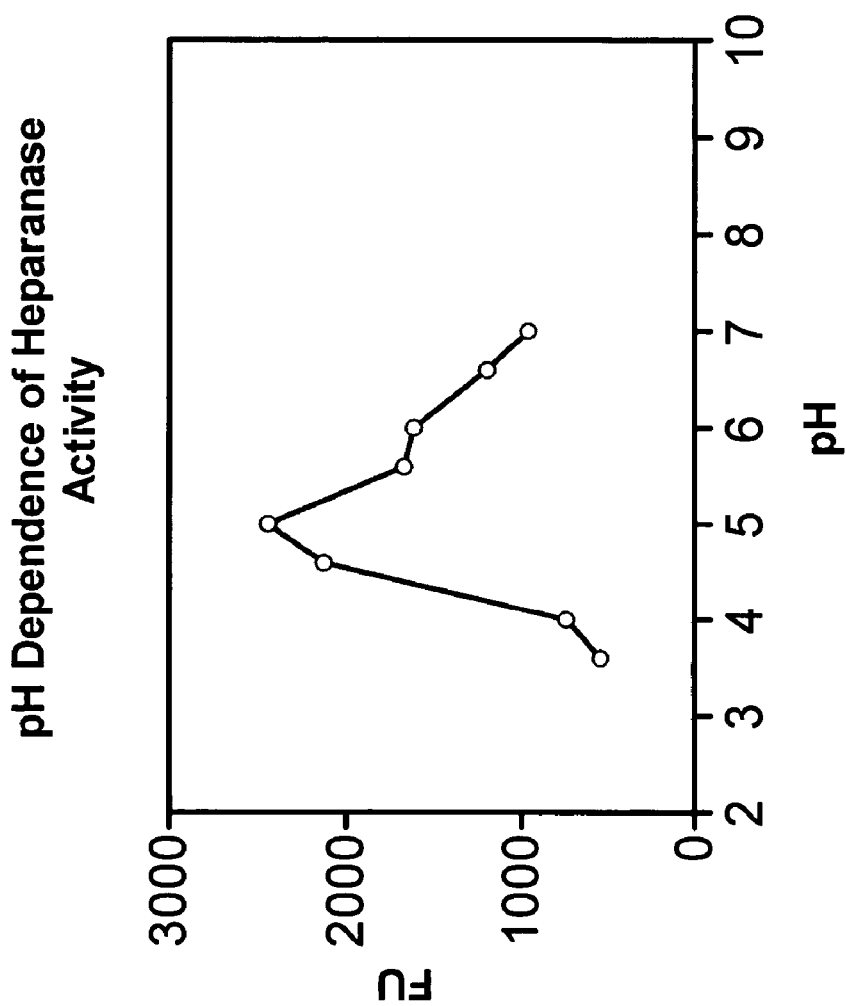
FIG. 8 graphically shows the pH dependence of heparanase activity.

FIG. 8 pH Dependence of Heparanase Activity.

FGF was coated onto microtiter plates and incubated with $F_2$FITC-HS as described. Crude heparanase was diluted into 50 mM citric acid-$Na_2HPO_4$ buffer at various pHs (3.6-7.0) containing 0.2 mg/ml BSA and 5 mM N-acetyl-mannosamine. Heparanase reaction was then carried out at various pHs at 37° C. for 1 hr. Bound $F_2$FITC-HS was also incubated with buffer at various pHs (no heparanase) and used as a background. Heparanase activity was calculated after subtracting background fluorescence.

FIG. 9 Signal and Background of $F_2$FITC-HS/FGF Assay on Zeiss uHTS.

$F_2$FITC-HS/FGF assay was run on Zeiss uHTS system for screening inhibitors. For each 384 well assay plate, wells in columns 1 and 2 contained only Assay Buffer (i.e. no heparanase or testing compounds). The average fluorescence intensity from those wells was used as a "background". Wells in columns 3 and 4 contained heparanase, but no testing compounds. The average fluorescence intensity from those wells was used as a "total signal". These two values were used for calculation of % inhibition by a specific compound (testing compounds were placed in wells from column 5 to 24). To check the quality of the screen, "total signal" and "background" from the screened plates were plotted. The X-axis represents Plate ID and the Y-axis represent fluorescence intensity. If the "total signal" for a particular plate is higher or lower than the mean plus or minus 2 times of standard deviations (M+/−2σ), that plate was retested.

FIG. 10 Z' Factor of $F_2$FITC-HS/FGF Assay on Zeiss uHTS.

Z' factor was calculated from each assay plate by the formula: Z' factor=1-3($\sigma_T$+$\sigma_B$)/($m_T$−$m_B$), where $m_T$=mean of total signal (wells in columns 3 and 4), $m_B$=mean of background (wells in columns 1 and 2), $\sigma_T$=standard deviation of total signal, and $\sigma_B$=standard deviation of background. To check the quality of the screen, Z' factors of the plates were plotted. The X-axis represents Plate ID and the Y-axis represent Z' factor. If the Z' factor for a particular plate was lower than the mean minus 2 times of standard deviations (M−2σ), the plate was retested. The Z' values, which ranged from about 0.3-0.7, indicate assay consistency and reproducibility.

FIG. 11 (A) Eu-HS Binding to FGF Coated Plates.

384 well plates were coated with FGF (0.75 μg/40 μl/well) followed by blocking with BSA as described. Plates were then incubated with various amounts of Eu-HS at 37° C. for 1 hr and washed with TBS. Bound Eu-HS was then eluted from plates with 0.1% SDS/TBS (40 μl/well). An aliquot (8 μl) was withdrawn and mixed with 60 μl of "Enhancement Solution" for TRF measurement.

(B) Heparanase Concentration Dependent Digestion of Eu-HS on FGF Coated Plates.

Eu-HS/FGF assay was carried out as described except that various amounts of purified heparanase were used.

FIG. 12 (A) $F_2$FITC-HS-Biotin Binding to SA Coated Plates.

384 well plates were coated with SA followed by blocking with BSA as described. Plates were then incubated with various amounts of $F_2$FITC-HS-biotin at 37° C. for 1 hr and washed with TBS. Bound $F_2$FITC-HS-biotin was then eluted from plates with 0.1% SDS/TBS (40 μl/well) and fluorescence was measured.

(B) Heparanase Concentration Dependent Digestion of $F_2$FITC-HS-Biotin on SA Coated Plates.

$F_2$FITC-HS-biotin/SA assay was carried out as described except that various amounts of purified heparanase were used.

FIG. 13 (A) Eu-HS-Biotin Binding to SA Coated Plates.

384 well plates were coated with SA followed by blocking with BSA as described. Plates were then incubated with various amounts of Eu-HS-biotin at 37° C. for 1 hr and washed with TBS. Bound Eu-HS-biotin was then eluted from plates with 0.1% SDS/TBS (40 μl/well). An aliquot (8 μl) was withdrawn and mixed with 60 μl of "Enhancement Solution" for TRF measurement.

(B) Heparanase Concentration Dependent Digestion of Eu-HS-Biotin on SA Coated Plates.

Eu-HS-biotin/SA assay was carried out as described except that various amounts of purified heparanase were used.

REFERENCES (1) Jackson, R. L., Busch, S. J., and Cardin, A. L. (1991) Glysosaminoglycans: Molecular properties, protein interactions and role in physiological processes. *Physiol. Rev.* 71 481-539.
(2) Kjellen, L. and Lindahl, U. (1991) Proteoglycans: structures and interactions. *Annu. Rev. Biochem.* 60, 443-475.
(3) Wight, T. N., Kinsella, M. G., and Qwarnstromn, E. E. (1992) The role of proteoglycans in cell adhesion, migration, and proliferation. *Curr. Opin. Cell Biol.* 4, 793-801.
(4) Ishai-Michaeli, R., Eldor, A., and Vlodavsky, I. (1990) Heparanase activity expressed by platelets, neutrophils and lymphoma cells releases active fibroblast growth factor from extracellular matrix. *Cell Reg.* 1, 833-842.
(5) Schlessinger, J., Lax, I., and Lemmon, M. (1995) Regulation of growth factor activation by proteoglycans: what is the role of the low affinity receptors? *Cell.* 83, 357-60.
(6) Najjam, S., Gibbs, R. V., Gordon, M. Y., and Rider, C. C. (1997) Characterization of human recombinant interleukin 2 binding to heparin and heparan sulfate using an ELISA approach. *Cytokine.* 9, 1013-22
(7) Eisenberg, S., Sehayek, E., Olivercrona, T., and Vlodavsky, I. (1992) Lipoprotein lipase enhances binding of lipoproteins to heparan sulfate on cell surfaces and extracellular matrix. *J. Clin. Invest.* 90, 2013-2021.
(8) Schulz, J. G., Megow, D., Reszka, R., Villringer, A., Einhaupl, K. M., and Dirnagl, U. (1998) Evidence that glypican is a receptor mediating beta-amyloid neurotoxicity in $PC_{12}$ cells. *Eur J Neurosci.* 10, 2085-93.
(9) Sewell, R. F., Brenchley, P. E., and Mallick, N. P. (1989) Human mononuclear cells contain an endoglycosidase specific for heparan sulfate glycosaminoglycan demonstrable with the use of a specific solid-phase metabolically radiolabelled substrate. *Biochem. J.* 264, 777-783.

References (Continued)
(10) Kosir, M. A., Quinn, C. C., Zukowski, K. L., Grignon, D. J., and Ledbetter, S. (1997) Human prostate carcinoma cells produce extracellular heparanase. *J. Surg. Res.* 67, 98-105.
(11) Godder, K., Vlodavsky, I., Eldor, A., Weksler, B. B., Haimovvitz-Friedman, A., and Fuks, Z. (1991) Heparanase activity in cultured endothelial cells. *J. Cell Physiol.* 148, 274-280.
(12) Bame, K. J. (1993) Release of heparan sulfate glycosaminoglycans from proteoglycans in Chinese hamster ovary cells does not require proteolysis of the core protein. *J. Biol. Chem.* 268, 19956-19964.
(13) Vlodavsky, I., Fuks, Z., Bar-Ner, M., Ariav, Y., and Schirrmacher, V. (1983) Lymphoma cell mediated degradation of sulfated proteoglycans in the subendothelial extracellular matrix relationship to tumor cell metastasis. *Cancer Res.* 43, 2704-2711.
(14) Vlodavsky, I., Eldor, A., Haimovitz-Friedman, A., Metzner, Y., Ishai-Michaeli, R., Lider, O., Naparstek, Y., Cohen, I. R., and Fuks, Z. (19=2) Expression of heparanase by platelets and circulating cells of the immune system:

possible involvement in diapedesis and extravasation. *Invasion Metastasis* 12, 112-127.

(15) Nakajima, M., Irimura, T., DiFerranta, D., DiFerranta, N., and Nicholson, G. L. (1983) Heparan sulfate degradation: relation to tumor invasion and metastatic properties of mouse B16 melanoma sublines. *Science* 220, 611-613.

(16) Ikuta, M., Podyma, K. A., Maruyama, K., Enomoto, S., Yanagishita, M. (2001) Expression of heparanase in oral cancer cell lines and oral cancer tissues. *Oral Oncol* 37, 177-184.

(17) Hanahan, D., and Folkman, J. (1996) Patterns and Emerging mechanisms of the angiogenic switch during tumorigenesis. *Cell,* 86, 353-364.

(18) Zetter, B. R. (1998) Angiogenesis and tumor metastasis. *Ann. Rev. Med.* 49, 407-424.

References (Continued)

(19) Nakajima, M., Irimura, T., and Nicholson, G. L. (1988) Heparanase and tumor metastasis. *J. Cell Biochem.* 36, 157-167.

(20) Vlodavsky, I., Mohsen, M., Lider, O., Svahn, C. M., Ekre, H. P., Vigoda, M., Ishai-Michaeli, R., Peretz, T. (1995) Inhibition of tumor metastasis by heparanase inhibiting species of heparin. *Invasion Metastasis* 14, 290-302.

(21) Parish, C. R., Coombe, D. R., Kakobsen, K. B., and Underwood, P. A. (1987) Evidence that sulphated polysaccharides inhibit tumor metastasis by blocking tumor cell-derived heparanase. *Int. J. Cancer* 40, 511-517.

(22) Parish, C. R., Freeman, C., Brown, K. J., Francis, D. J., and Cowden, W. B. (1999) Identification of sulfated oligosaccharide-based inhibitors of tumor growth and metastasis using novel in vitro assays for angiogenesis and heparanase activity. *Cancer Res.* 59, 3433-3441.

(23) Lider, O., Baharav, E., Mekori, Y. A., Miller, T., Naparstek, Y., Vlodavsky, I., and Cohen, I. R. (1989) Suppression of experimental autoimmune diseases and prolongation of allograft survival by treatment of animals with low doses of heparins. *J. Clin. Invest.* 83, 752-756.

(24) Willenborg, D. O., and Parish, C. R. (1988) Inhibition of allerhic encephalomyelitis in rats by treatment with sulfated polysaccharides. *J. Immunol.* 140, 3401-3405.

(25) Prats H, Kaghad M, Prats A C, Klagsbrun M, Lelias J M, Liauzun P, Chalon P, Tauber J P, Amalric F, Smith J A, et al. (1989) High molecular mass forms of basic fibroblast growth factor are initiated by alternative CUG codons. *Proc Natl Acad Sci USA* 86, 1836-40.

(26) Toyoshima, M., and Nakajima, M. (1999) Human heparanase-purification, characterization, cloning, and expression. *J. Biol. Chem.* 274, 24153-24160.

(27) Freeman, C., and Parish, C. R. (1997) A rapid quantitative assay for the detection of mammalian heparanase activity. *Biochem. J.* 325, 229-237.

References (Continued)

(28) Freeman, C. and Parish, C. (1998) Human platelet heparanase: purification, characterization and catalytic activity. *Biochem. J.* 330, 1341-1350.

(29) Hemmila, I., Dakubu, S., Mukkala, V. M., Siitari, H., Lovgren, T. (1984) Europium as a label in time-resolved immunofluorometric assays. *Anal. Biochem.* 137, 335-343.

(30) Hemmila, I., and Webb, S (1997) Time-resolved fluorometry: An overview of the labels and core technologies for drug screening applications. *Drug Discovery Today* 2, 373-381.

(31) Folkman, J. (1995) Angiogenesis in cancer, vascular, rheumatoid and other diseases. *Nat. Med.* 1, 27-31.

(32) Satoh, A., Fukui, E., Yoshino, S., Shinoda, M., Kojima, K., and Matsumoto, I. (1999) Comparison of methods of immobilization to enzyme-linked immunosorbent assay plates for the detection of sugar chains. *Anal. Biochem.* 275, 231-235.

(33) Ben-Artzi, H., Ayal-Hershkovitz, M., Vlodavsky, I., Pecker, I., Peleg, Y., and Miron, D. (2001) Methods of screening for potential anti-metastatic and anti-inflammatory agents using mammalian heparanase as a probe. U.S. Pat. No. 6,190,875.

(34) Bartlett, et al. (1995) Comparative analysis of the ability of leukocytes, endothelial cells and platelets to degrade the subendothelial basement membrane: Evidence for cytokine dependence and detection of a novel sulfatase. *Immunol. Cell Biol.* 73: 113-124.

(35) Vlodavsky et al. (1992) Expression of heparanase by platelets and circulating cells of the immune system: Possible involvement in diapedesis and extravasation. *Invasion Metastasis* 12: 112-127.

(36) Ishai-Michaeli R., et al. (1992) Importance of size and sulfation of heparin in release of βFGF from the vascular endothelium and extracellular matrix. *Biochemistry* 31: 2080-2088.

What is claimed is:

1. A method for testing an agent for its ability to inhibit the binding between fibroblast growth factor (FGF) and heparan sulfate which is labeled comprising interacting the agent and the labeled heparan sulfate in a solution with immobilized FGF and detecting the presence or absence of the labeled heparan sulfate in the solution to determine whether or not the agent has the ability to inhibit the binding between FGF and the labeled heparan sulfate.

* * * * *